United States Patent
Türk et al.

(10) Patent No.: US 9,648,873 B2
(45) Date of Patent: May 16, 2017

(54) ALKOXYLATED HYPERBRANCHED POLYCARBONATES FOR SOLUBILIZING POORLY SOLUBLE ACTIVE INGREDIENTS

(75) Inventors: Holger Türk, Mannheim (DE); Monika Haberecht, Ludwigshafen (DE); Bernd Bruchmann, Freinsheim (DE); Andreas Kunst, Ludwigshafen (DE); Daniel Schönfelder, Hong Kong (CN); Michael Ishaque, Mannheim (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 13/514,332

(22) PCT Filed: Dec. 3, 2010

(86) PCT No.: PCT/EP2010/068791
§ 371 (c)(1),
(2), (4) Date: Aug. 16, 2012

(87) PCT Pub. No.: WO2011/069895
PCT Pub. Date: Jun. 16, 2011

(65) Prior Publication Data
US 2012/0309629 A1   Dec. 6, 2012

(30) Foreign Application Priority Data
Dec. 9, 2009   (EP) ..................................... 09178507

(51) Int. Cl.
*A01N 25/30* (2006.01)
*C08G 64/02* (2006.01)

(52) U.S. Cl.
CPC ......... *A01N 25/30* (2013.01); *C08G 64/0216* (2013.01)

(58) Field of Classification Search
CPC ............................ A01N 25/30; C08G 64/0216
USPC ...... 424/486; 504/358, 360, 362; 514/772.7; 525/403, 462; 528/370, 405, 418, 421
See application file for complete search history.

(56) References Cited

U.S. PATENT DOCUMENTS

| 2008/0167430 A1 | 7/2008 | Bruchmann et al. |
| 2009/0099319 A1 | 4/2009 | Stumbe et al. |
| 2011/0105333 A1* | 5/2011 | Israels et al. ................ 504/360 |
| 2012/0054920 A1 | 3/2012 | Tuerk et al. |

FOREIGN PATENT DOCUMENTS

| DE | 102005009166 | 8/2006 |
| WO | WO 2007/125028 | 11/2007 |
| WO | WO 2009/021986 | 2/2009 |
| WO | WO 2009021986 A1 * | 2/2009 |
| WO | WO 2010/130599 | 11/2010 |

OTHER PUBLICATIONS

Akzo Nobel, HLB & Emulsification: Description of Hydrophile, Liphile Balance and use of HLB in Producing Emulsions, 2011, p. 1-15.*
English language translation of the International Preliminary Report on Patentability dated Mar. 19, 2012, from corresponding International Application No. PCT/EP2010/068791, filed Dec. 3, 2010.
International Search Report completed Feb. 14, 2011, in International Application No. PCT/EP2010/068791, filed Dec. 3, 2010.
Griffin, "Calculation of HLB Values of Non-Ionic Surfactants", Journal of the Society of Cosmetic Chemists, pp. 249-256, presented at the May 14, 1954 Meeting in New York City, Atlas Power Company, Wilmington, DE.

* cited by examiner

*Primary Examiner* — Robert Jones, Jr.
(74) *Attorney, Agent, or Firm* — Brinks Gilson & Lione

(57) ABSTRACT

The present invention provides a composition comprising an active ingredient whose solubility in water at 20° C. is not more than 10 g/L, and an amphiphile comprising an alkoxylated hyperbranched polycarbonate, wherein the polycarbonate comprises an alcohol which is a trifunctional or higher polyfunctional polyetherol based on a $C_3$-$C_{12}$ alkylene oxide and an alcohol which has at least three OH groups. Likewise provided is an amphiphile comprising the polycarbonate, and a process for preparing the amphiphile. The invention further relates to the use of the amphiphile for solubilizing an active ingredient whose solubility in water at 20° C. is not more than 10 g/L, in aqueous solutions, and a method of controlling phytopathogenic fungi and/or unwanted plant growth and/or unwanted insect or mite infestation and/or of regulating the growth of plants.

11 Claims, No Drawings

ALKOXYLATED HYPERBRANCHED POLYCARBONATES FOR SOLUBILIZING POORLY SOLUBLE ACTIVE INGREDIENTS

This application is a National Stage application of International Application No. PCT/EP2010/068791, filed Dec. 3, 2010, the entire contents of which is hereby incorporated herein by reference. This application also claims priority under 35 U.S.C. §119 to European Patent Application No. 09178507.1, filed Dec. 9, 2009, the entire contents of which is hereby incorporated herein by reference.

The present invention provides a composition comprising an active ingredient whose solubility in water at 20° C. is not more than 10 g/L, and an amphiphile comprising an alkoxylated hyperbranched polycarbonate, wherein the polycarbonate comprises an alcohol (B1) which is a trifunctional or higher polyfunctional polyetherol based on a $C_3$-$C_{12}$ alkylene oxide and an alcohol which has at least three OH groups. Likewise provided is an amphiphile comprising the polycarbonate, and a process for preparing the amphiphile. The invention further relates to the use of the amphiphile for solubilizing an active ingredient whose solubility in water at 20° C. is not more than 10 g/L, in aqueous solutions, and a method of controlling phytopathogenic fungi and/or unwanted plant growth and/or unwanted insect or mite infestation and/or of regulating the growth of plants. Combinations of preferred features with other preferred features are embraced by the present invention.

Many cases require hydrophobic active ingredients to be solubilized in water without causing any chemical change to the active ingredient in question as such. For this purpose it is possible, for example, to prepare an emulsion, with the active ingredient in question being situated in the oil phase of the emulsion. For many active pharmaceutical ingredients or crop protection agents, however, especially those which are to be transported with a body fluid or in the sap of a plant, a procedure of this kind is not possible. Under the action of high shearing forces, emulsions may break. Moreover, sterilizing while maintaining the emulsion is in many cases not possible.

Compositions comprising an amphiphile and a sparingly soluble active ingredient are common knowledge:

WO 2007/125028 discloses a method of solubilizing hydrophobic active ingredients in an aqueous medium using as an auxiliary a hyperbranched polymer obtainable by preparing a hyperbranched polyester on the basis of a dicarboxylic, tricarboxylic or tetracarboxylic acid and a diol or triol and reacting the polyester with a polyalkylene oxide unit.

WO 2009/021986 discloses a seed dressing comprising an active ingredient and a hyperbranched polymer, which may be a hyperbranched polycarbonate, for example.

A disadvantage of the known amphiphiles for solubilizing hydrophobic active ingredients in aqueous media is that they are able to solubilize only small amounts of active ingredient. Moreover, the amphiphiles themselves are often not water-soluble or water-dispersible, and so are not suitable for solubilization in aqueous media. Polyester-containing amphiphiles have the disadvantage, moreover, that they are themselves in some cases sensitive to hydrolysis, particularly as a result of the terminal acid groups present.

Polycarbonates are typically obtained from the reaction of alcohols or phenols with phosgene or from the reaction of alcohols or phenols with dialkyl or diaryl carbonates. Important industrially are aromatic polycarbonates which are prepared, for example, from bisphenols; in terms of market volume, aliphatic polycarbonates have to date played a minor part. The aromatic or aliphatic polycarbonates described in the literature are generally of linear construction or constructed with only a low degree of branching. Hyperbranched polycarbonates as well, however, are common knowledge: WO 2006/089940 discloses water-emulsifiable hyperbranched polycarbonates which at least in part are reacted directly with a monofunctional polyalkylene oxide polyether alcohol.

It was an object of the present invention to find an alternative amphiphile suitable for solubilizing sparingly soluble active ingredients in an aqueous medium. A further object was to find an amphiphile which is able to solubilize very high quantities of active ingredient, especially active agrochemical ingredient. Moreover, the amphiphile ought itself to be water-soluble or water-dispersible. A further object, finally, was to find an amphiphile which is less sensitive to hydrolysis than polyesters.

The object has been achieved by means of a composition comprising an active ingredient whose solubility in water at 20° C. is not more than 10 g/L, and an amphiphile comprising an alkoxylated hyperbranched polycarbonate, wherein the polycarbonate comprises an alcohol (B1) which is a trifunctional or higher polyfunctional polyetherol based on a $C_3$-$C_{12}$ alkylene oxide and an alcohol which has at least three OH groups.

The solubility of the active ingredient in water at 20° C. is not more than 10 g/L, preferably not more than 2 g/l, more preferably not more than 0.5 g/l, and especially not more than 0.1 g/l. The composition may comprise one or more different active ingredients. Examples of active ingredients are active agrochemical ingredients, active cosmetic ingredients, active pharmaceutical ingredients or nutritional supplements (such as vitamins and carotenoids). Preferred active ingredients are active agrochemical ingredients.

Examples of active cosmetic ingredients are cosmetic oils, aromas and flavors, vitamins or UV absorbers. Cosmetic oils include peanut oil, jojoba oil, coconut oil, almond oil, olive oil, palm oil, castor oil, soybean oil, wheatgerm oil, or essential oils such as dwarf pine oil, lavender oil, rosemary oil, spruce needle oil, pine needle oil, eucalyptus oil, peppermint oil, sage oil, bergamot oil, turpentine oil, balm oil, juniper oil, lemon oil, anise oil, cardamom oil, camphor oil, etc., or mixtures thereof. UV absorbers include 2-hydroxy-4-methoxybenzophenone, 2,2',4,4'-tetrahydroxybenzophenone, 2,2'-dihydroxy-4,4'-dimethoxybenzophenone, 2,4-dihydroxybenzophenone, 2'-ethylhexyl 2-cyano-3,3-diphenylacrylate, 2,4,6-trianilino-p-(carbo-2'-ethylhexyl-1'-oxy)-1,3,5-triazine, 3-(4-methoxybenzylidene)camphor, 2-ethylhexyl N,N-dimethyl-4-aminobenzoate, 3,3,5-trimethylcyclohexyl salicylate, 4-isopropyldibenzoylmethane, 2-ethylhexyl p-methoxycinnamate, and 2-isoamyl p-methoxycinnamate, and mixtures thereof.

Examples of aromas and flavors are as described in WO 01/49817 or in "Flavors and Fragrances", Ullmann's Encyclopedia of Industrial Chemistry, Wiley-VCH, 2002, hereby incorporated by reference.

Examples of vitamins are vitamins, provitamins and vitamin precursors form the groups A, C, E, and F, more particularly 3,4-didehydroretinol, beta-carotene (provitamin of vitamin A), ascorbic acid (vitamin C), and the palmitic esters, glucosides or phosphates of ascorbic acid, tocopherols, more particularly alpha-tocopherol and its esters, such as the acetate, nicotinate, phosphate, and succinate, for example; and also vitamin F, which is understood to constitute essential fatty acids, particularly linoleic acid, linolenic acid, and arachidonic acid.

Examples of active pharmaceutical ingredients include the following: benzodiazepines, antihypertensives, vitamins, cytostatics, especially taxol, anesthetics, neuroleptics, antidepressants, antivirals, such as anti-HIV agents, antibiotics, antimycotics, antidementia drugs, fungicides, chemotherapeutic agents, urologicals, platelet aggregation inhibitors, sulfonamides, spasmolytics, hormones, immunoglobulins, sera, thyroid therapeutics, psychoactive drugs, anti-Parkinson agents and other anti-hyperkinetics, ophthalmologicals, neuropathy products, calcium metabolism regulators, muscle relaxants, anesthetics, lipid-lowering agents, hepatotherapeutics, coronary agents, cardiac agents, immunotherapeutics, regulatory peptides and their inhibitors, hypnotics, sedatives, gynaecologicals, gout remedies, fibrinolytics, enzyme products and transport proteins, enzyme inhibitors, emetics, blood flow stimulators, diuretics, diagnostic aids, corticoids, cholinergics, biliary therapeutics, antasthmatics, bronchodilators, beta-receptor blockers, calcium antagonists, ACE inhibitors, arteriosclerosis remedies, antiinflammatories, anticoagulants, antihypotensives, antihypoglycemics, antihypertensives, antifibrinolytics, antiepileptics, antiemetics, antidotes, antidiabetics, antiarrythmics, antianemics, antiallergics, antelmintics, analgesics, analeptics, aldosterone antagonists, slimming agents.

The term "active agrochemical ingredients" (also called pesticides below) refers to at least one active ingredient selected from the group of insecticides, insecticides, nematicides, herbicides, safeners and/or growth regulators. Preferred pesticides are fungicides, insecticides and herbicides, especially insecticides. Mixtures of pesticides from two or more of the aforementioned classes can also be used. The skilled person is familiar with such pesticides, which can be found in Pesticide Manual, 14th Ed. (2006), The British Crop Protection Council, London, for example. Suitable insecticides are insecticides from the class of the carbamates, organophosphates, organochlorine insecticides, phenylpyrazoles, pyrethroids, neonicotinoids, spinosins, avermectins, milbemycins, juvenile hormone analogues, alkyl halides, organotin compounds, nereistoxin analogues, benzoylureas, diacylhydrazines, METI acaricides, and also insecticides such as chloropicrin, pymetrozine, flonicamid, clofentezine, hexythiazox, etoxazole, diafenthiuron, propargite, tetradifon, chlorfenapyr, DNOC, buprofezine, cyromazine, amitraz, hydramethylnon, acequinocyl, fluacrypyrim, rotenone or derivatives thereof. Suitable fungicides are fungicides from the classes of the dinitroanilines, allylamines, anilinopyrimidines, antibiotics, aromatic hydrocarbons, benzenesulfonamides, benzimidazoles, benzisothiazoles, benzophenones, benzothiadiazoles, benzotriazines, benzylcarbamates, carbamates, carboxamides, carboxylic acid amdide chloronitriles, cyanoacetamide oximes, cyanoimidazoles, cyclopropanecarboxamides, dicarboximides, dihydrodioxazines, dinitrophenylcrotonates, dithiocarbamates, dithiolanes, ethylphosphonates, ethylaminothiazole carboxamides, guanidines, hydroxyl(2-amino)pyrimidines, hydroxyanilides, imidazoles, imidazolinones, inorganics, isobenzofuranones, methoxyacrylates, methoxycarbamates, morpholines, N-phenylcarbamates, oxazolidinediones, oximinoacetates, oximinoacetamides, peptidylpyrimidine nucleosides, phenylacetamides, phenylamides, phenylpyrroles, phenylureas, phosphonates, phosphorothiolates, phthalamic acids, phthalimides, piperazines, piperidines, propionamides, pyridazinones, pyridines, pyridinylmethylbenzamides, pyrimidinamines, pyrimidines, pyrimidinone hydrazones, pyrroloquinolinones, quinazolinones, quinolines, quinones, sulfamides, sulfamoyltriazoles, thiazolecarboxamides, thiocarbamates, thiophanates, thiophenecarboxamides, toluamides, triphenyltin compounds, triazines, triazoles. Suitable herbicides are herbicides from the classes of the acetamides, amides, aryloxyphenoxypropionates, benzamides, benzofuran, benzoic acids, benzothiadiazinones, bipyridylium, carbamates, chloroacetamides, chlorocarboxylic acids, cyclohexanediones, dinitroanilines, dinitrophenol, diphenyl ethers, glycines, imidazolinones, isoxazoles, isoxazolidinones, nitriles, N-phenylphthalimides, oxadiazoles, oxazolidinediones, oxyacetamides, phenoxycarboxylic acids, phenylcarbamates, phenylpyrazoles, phenylpyrazolines, phenylpyridazines, phosphinic acids, phosphoroamidates, phosphorodithioates, phthalamates, pyrazoles, pyridazinones, pyridines, pyridinecarboxylic acids, pyridinecarboxamides, pyrimidinediones, pyrimidinyl(thio)benzoates, quinolinecarboxylic acids, semicarbazones, sulfonylaminocarbonyltriazolinones, sulfonylureas, tetrazolinones, thiadiazoles, thiocarbamates, triazines, triazinones, triazoles, triazolinones, triazolocarboxamides, triazolopyrimidines, triketones, uracils, ureas.

In one embodiment the pesticide comprises an insecticide, and preferably the pesticide is composed of at least one insecticide. Preferred insecticides are fipronil, allethrin, alpha-cypermethrin, beta-cyfluthrin, bifenthrin, bioallethrin, 4-chloro-2-(2-chloro-2-methylpropyl)-5-[(6-iodo-3-pyridinyl)methoxy]-3(2H)-pyridazinone (CAS RN: 120955-77-3), chlorfenapyr, chlorpyrifos, cyfluthrin, cyhalothrin, cypermethrin, deltamethrin, etofenprox, fenoxycarb, flufenoxuron, hydramethylnon, metaflumizone, permethrin, pyriproxifen, silafluofen, tebufenocide, and tralomethrin. Particularly preferred insecticides are fipronil, alpha-cypermethrin, bifenthrin, chlorfenapyr, cyfluthrin, cypermethrin, deltamethrin, etofenprox, hydramethylnon, metaflumizone, permethrin. Especially preferred insecticides are fipronil, alpha-cypermethrin, deltamethrin, chlorfe-napyr, hydramethylnon, and metaflumizone. An especially preferred insecticide is fipronil. In another embodiment the pesticide comprises a fungicide, and preferably the pesticide is composed of at least one fungicide. Preferred fungicides are pyraclostrobin, metconazole, and epoxiconazole. In another embodiment the pesticide comprises a herbicide, and preferably the pesticide is composed of at least one herbicide. In another embodiment the pesticide comprises a growth regulator, and preferably the pesticide is composed of at least one growth regulator.

The composition of the invention comprises typically 0.1% to 70% by weight of active ingredient, preferably 1% to 50% by weight, more particularly 3% to 30% by weight, based on the composition.

Amphiphiles typically comprise at least one polar (hydrophilic) moiety and at least one apolar (hydrophobic) moiety. Typical amphiphiles are fatty acids, surfactants, and phospholipids. The composition may comprise one or more different amphiphiles. The amphiphile is preferably an alkoxylated hyperbranched polycarbonate, wherein the polycarbonate comprises an alcohol (B1) which is a trifunctional or higher polyfunctional polyetherol based on a $C_3$-$C_{12}$ alkylene oxide and an alcohol which has at least three OH groups.

By hyperbranched polycarbonates for the purposes of this invention are meant noncrosslinked macromolecules having hydroxyl and carbonate or carbamoyl chloride groups, which may be both structurally and molecularly nonuniform. On the one hand they may be synthesized starting from a central molecule in the same way as for dendrimers but, in contrast to the latter, with a nonuniform chain length of the branches. Hyperbranched polymers are therefore to be differentiated from dendrimers (U.S. Pat. No. 6,399,048). For the purposes of the present invention, hyperbranched polymers do not comprise dendrimers. On the other hand, the hyperbranched polymers may also be of linear construction, with functional, branched side groups, or else, as a combination of the two extremes, may include linear and branched molecule moieties. For the definition of dendrimers and hyperbranched polymers see also P. J. Flory, J. Am. Chem. Soc. 1952, 74, 2718 and H. Frey et al., Chem. Eur. J. 2000, 6, 2499. By "hyperbranched" in the context of the present invention is meant that the degree of branching (DB), in other words the ratio of the sum of the average number of dendritic linkages plus the average number of end groups to the sum of the average number of dendritic and linear linkages plus the average number of end groups, per molecule, multiplied by 100, is 10% to 99.9%, preferably 20% to 99%, more preferably 20% to 95%. By "dendrimeric" in the context of the present invention is meant that the degree of branching is 99.9%-100%. For the definition of the degree of branching see H. Frey et al., Acta Polym. 1997, 48, 30.

It is an advantage of the present invention that the polycarbonates of the invention are noncrosslinked. "Noncrosslinked" for the purposes of this specification means that the degree of crosslinking present is less than 15% by weight, preferably less than 10% by weight, determined via the insoluble fraction of the polymer. The insoluble fraction of the polymer was determined by four-hour extraction with the same solvent as used for the gel permeation chromatography for determining the molecular weight distribution of the polymers, i.e., tetrahydrofuran, dimethylacetamide or hexafluoroisopropanol, according to which solvent has the better solvency for the polymer, in a Soxhlet apparatus and, after drying of the residue to constant weight, by weighing of the residue remaining.

The hyperbranched polycarbonate is typically obtainable by
a) preparing a condensation product (K) by reacting an organic carbonate (A) or a phosgene derivative with an alcohol (B1) which has at least three hydroxyl groups, and
b) intermolecularly converting K to the hyperbranched polycarbonate, the quantitative ratio of the OH groups to the carbonate or phosgene groups being selected such that K has an average of either i) one carbonate or carbamoyl chloride group and more than one OH group, or ii) one OH group and more than one carbonate or carbamoyl group. The polycarbonate is preferably obtained in this way.

The condensation product (K) can be prepared using an organic carbonate (A) or a phosgene derivative. Examples of suitable phosgene derivatives are phosgene, diphosgene or triphosgene, preferably phosgene. It is preferred to use an organic carbonate.

The radicals R in the organic carbonates (A) of the general formula $RO[(CO)O]_nR$ that are used as starting material are each independently of one another a straight-chain or branched aliphatic, aromatic/aliphatic (araliphatic) or aromatic hydrocarbon radical having 1 to 20 C atoms. The two radicals R may also be joined to one another to form a ring. The two radicals R may be the same or different; they are preferably the same. The radical in question is preferably an aliphatic hydrocarbon radical and more preferably a straight-chain or branched alkyl radical having 1 to 5 C atoms, or a substituted or unsubstituted phenyl radical. R in this case is a straight-chain or branched, preferably straight-chain (cyclo)aliphatic, aromatic/aliphatic or aromatic, preferably (cyclo)aliphatic or aromatic, more preferably aliphatic hydrocarbon radical having 1 to 20 C atoms, preferably 1 to 12, more preferably 1 to 6, and very preferably 1 to 4 carbon atoms. Examples of such radicals are methyl, ethyl, isopropyl, n-propyl, n-butyl, isobutyl, sec-butyl, tert-butyl, n-hexyl, n-heptyl, n-octyl, n-decyl, n-dodecyl, n-tetradecyl, n-hexadecyl, n-octadecyl, n-eicosyl, 2-ethylhexyl, cyclopentyl, cyclohexyl, cyclooctyl, cyclododecyl, phenyl, o- or p-tolyl or naphthyl. Methyl, ethyl, n-butyl, and phenyl are preferred. These radicals R may be the same or different; they are preferably the same. The radicals R may also be joined to one another to form a ring. Examples of divalent radicals R of this kind are 1,2-ethylene, 1,2-propylene, and 1,3-propylene. Generally speaking, n is an integer from 1 to 5, preferably from 1 to 3, more preferably from 1 to 2. The carbonates may preferably be simple carbonates of the general formula RO(CO)OR, i.e. n in this case is 1.

Examples of suitable carbonates comprise aliphatic, aromatic/aliphatic or aromatic carbonates such as ethylene carbonate, 1,2- or 1,3-propylene carbonate, diphenyl carbonate, ditolyl carbonate, dixylyl carbonate, dinaphthyl carbonate, ethyl phenyl carbonate, dibenzyl carbonate, dimethyl carbonate, diethyl carbonate, di-n-propyl carbonate, di-n-butyl carbonate, diisobutyl carbonate, dipentyl carbonate, dihexyl carbonate, dicyclohexyl carbonate, diheptyl carbonate, dioctyl carbonate, didecyl carbonate or didodecyl carbonate. Examples of carbonates in which n is greater than 1 comprise dialkyl dicarbonates, such as di-tert-butyl dicarbonate, or dialkyl tricarbonates such as di-tert-butyl tricarbonate. One preferred aromatic carbonate is diphenyl carbonate. Preference is given to aliphatic carbonates, more particularly those in which the radicals comprise 1 to 5 C atoms, such as dimethyl carbonate, diethyl carbonate, di-n-propyl carbonate, di-n-butyl carbonate or diisobutyl carbonate, for example. Diethyl carbonate is especially preferred.

The hyperbranched polycarbonate typically comprises an alcohol (B1) which is a trifunctional or higher-functionality polyetherol based on a $C_3$-$C_{12}$ alkylene oxide and an alcohol which has at least three OH groups. Suitable alcohols, which have at least three OH groups may be branched or unbranched, substituted or unsubstituted, and have 3 to 26 carbon atoms. It is preferably an aliphatic alcohol. Examples of compounds having at least three OH groups comprise glycerol, trimethylolmethane, trimethylolethane, trimethylolpropane (TMP), di-TMP, trimethylolbutane, 1,2,4-butantriol, 1,2,3-hexanetriol, 1,2,4-hexanetriol, tris(hydroxymethyl)amine, tris(hydroxyethyl)amine, tris(hydroxypropyl)amine, pentaerythritol, dipentaerythritol, diglycerol, triglycerol, polyglycerols, tris(hydroxymethyl) isocyanurate, tris(hydroxyethyl) isocyanurate, phloroglucinol, trihydroxytoluene, trihydroxydimethylbenzene, phloroglucides, hexahydroxybenzene, 1,3,5-benzenetrimethanol, 1,1,1-tris(4'-hydroxyphenyl)methane, 1,1,1-tris(4'-hydroxyphenyl)ethane, sugars, for example glucose, sugar derivatives, for example sorbitol, mannitol, diglycerol, threitol, erythritol, adonitol (ribitol), arabitol (lyxitol), xylitol, dulcitol (galactitol), maltitol, isomalt, or polyesterol. Preferred alcohols, which have at least three OH groups are glycerol, trimethylolethane, trimethylolpropane, 1,2,4-butanetriol, 1,2,3-hexanetriol, 1,2,4-hexanetriol, pentaerythritol, more preferably glycerol or trimethylolpropane. Preferred $C_3$-$C_{12}$ alkylene oxides include propylene oxide, butylene oxide, pentylene oxide and mixtures thereof, more preferably propylene oxide. The trifunctional or higher-functionality polyetherols usually comprise at least three, preferably three to 30, more preferably 3 to 20 $C_3$-$C_{12}$ alkylene oxide molecules in polymerized form. A particularly preferred alcohol (B1) is a trifunctional polyetherol based on glycerol, trimethylolethane, trimethylolpropane, 1,2,4-butanetriol and/or pentaerythritol, and propylene oxide, where the polyetherol comprises at least three, preferably three to 30, more preferably three to 20, molecules of propylene oxide in polymerized form. The $C_3$-$C_{12}$ alkylene oxide molecules which are present in polymerized form in the polyetherol may be linked to the polyetherol via one or more of the alcohol groups of the polyetherol. The $C_3$-$C_{12}$ alkylene oxide molecules may form one or more chains of polymerized $C_3$-$C_{12}$ alkylene oxide molecules. The alcohol (B1) is typically obtainable by polymerization of the $C_3$-$C_{12}$ alkylene oxide molecules onto the polyetherol. As a result, the $C_3$-$C_{12}$ alkylene oxide molecules are attached onto the polyether molecule by polymerization usually in statistical distribution.

In addition to the alcohol (B1), the polycarbonate may have a difunctional alcohol (B2) as a forming component, with the proviso that the mean OH functionality of all alcohols B used together is greater than 2. The alcohols (B1) and (B2) are referred to here together as (B). Suitable difunctional alcohols B2 include diethylene glycol, triethylene glycol, 1,2- and 1,3-propanediol, dipropylene glycol, tripropylene glycol, neopentyl glycol, 1,2-, 1,3- and 1,4-butanediol, 1,2-, 1,3- and 1,5-pentanediol, 1,6-hexanediol, 1,2- or 1,3-cyclopentanediol, 1,2-, 1,3- or 1,4-cyclohexanediol, 1,1-, 1,2-, 1,3- or 1,4-cyclohexanedimethanol, bis(4-hydroxycyclohexyl)methane, bis(4-hydroxycyclohexyl)ethane, 2,2-bis(4-hydroxycyclohexyl)propane, 1,1'-bis(4-hydroxyphenyl)-3,3,5-trimethylcyclohexane, resorcinol, hydroquinone, 4,4'-dihydroxybiphenyl, bis(4-hydroxyphenyl)sulfide, bis(4-hydroxyphenyl)sulfone, bis(hydroxymethyl)benzene, bis(hydroxymethyl)toluene, bis(p-hydroxyphenyl)methane, bis(p-hydroxyphenyl)ethane, 2,2-bis(p-hydroxyphenyl)propane, 1,1-bis(p-hydroxyphenyl)cyclohexane, dihydroxybenzophenone, difunctional polyetherpolyols based on ethylene oxide, propylene oxide, butylene oxide, pentylene oxide or mixtures thereof, polytetrahydrofuran having a molar mass of 162 to 2000, polycaprolactone or polyesterols based on diols and dicarboxylic acids. Preferred difunctional alcohols (B2) are difunctional polyetherpolyols based on ethylene oxide, propylene oxide, butylene oxide, pentylene oxide or mixtures thereof, and polyesterols based on diols and dicarboxylic acids.

The diols serve for fine adjustment of the properties of the polycarbonate. If difunctional alcohols are used, the ratio of difunctional alcohols (B2) to the at least trifunctional alcohols (B1) is fixed by the person skilled in the art according to the desired properties of the polycarbonate. In general, the amount of the alcohol(s) (B2) is 0 to 50 mol % based on the total amount of all alcohols (B1) and (B2) together. The amount is preferably 0 to 35 mol %, more preferably 0 to 25 mol % and most preferably 0 to 10 mol %.

The reaction of phosgene, diphosgene or triphosgene with the alcohol or alcohol mixture is generally effected with elimination of hydrogen chloride; the reaction of the carbonates with the alcohol or alcohol mixture to give the high-functionality hyperbranched polycarbonate is effected with elimination of the monofunctional alcohol or phenol from the carbonate molecule.

After this reaction, i.e., without any further modification, the hyperbranched polycarbonate has high-functionality termination with hydroxyl groups and with carbonate groups or carbamoyl chloride groups. A high-functionality polycarbonate is understood in the context of this invention to mean a product which, as well as the carbonate groups which form the polymer skeleton, additionally has, in terminal or lateral position, at least three, preferably at least four and more preferably at least six functional groups. The functional groups are carbonate groups or carbamoyl chloride groups and/or OH groups. There is in principle no upper limit in the number of terminal or lateral functional groups, but products with a very high number of functional groups may have undesired properties, for example high viscosity or poor solubility. The high-functionality polycarbonates of the present invention usually have not more than 500 terminal or lateral functional groups, preferably not more than 100 terminal or lateral functional groups.

In the preparation of the high-functionality polycarbonates, it is necessary to adjust the ratio of the compounds comprising OH groups to phosgene or carbonate (A) such that the resulting simplest condensation product (known hereinafter as condensation product (K)) comprises an average of either i) one carbonate or carbamoyl chloride group and more than one OH group or ii) one OH group and more than one carbonate or carbamoyl chloride group, preferably an average of either i) one carbonate or carbamoyl chloride group and at least two OH groups or ii) one OH group and at least two carbonate or carbamoyl chloride groups.

It may additionally be advisable, for fine adjustment of the properties of the polycarbonate, to use at least one difunctional carbonyl-reactive compound (A1). This is understood to mean those compounds which have two carbonate and/or carboxyl groups. Carboxyl groups may be carboxylic acids, carbonyl chlorides, carboxylic anhydrides or carboxylic esters, preferably carboxylic anhydrides or carboxylic esters and more preferably carboxylic esters. If such difunctional compounds (A1) are used, the ratio of (A1) to the carbonates or phosgenes (A) is fixed by the person skilled in the art according to the desired properties of the polycarbonate. In general, the amount of the difunctional compound(s) (A1) is 0 to 40 mol % based on the total amount of all carbonates/phosgenes (A) and compounds (A1) together. Preferably the amount is 0 to 35 mol %, more preferably 0 to 25 mol %, and very preferably 0 to 10 mol %. Examples of compounds (A1) are dicarbonates or dicarbamoyl chlorides of diols, examples of which are ethylene glycol, 1,2-propanediol, 1,3-propanediol, 1,1-dimethylethane-1,2-diol, 2-butyl-2-ethyl-1,3-propanediol, 2-ethyl-1,3-propanediol, 2-methyl-1,3-propanediol, neopentyl glycol, neopentyl glycol hydroxypivalate, 1,2-, 1,3- or 1,4-butanediol, 1,6-hexanediol, 1,10-decanediol, bis(4-hydroxycyclohexane)isopropylidene, tetramethylcyclobutanediol, 1,2-, 1,3- or 1,4-cyclohexanediol, cyclooctanediol, norbornanediol, pinanediol, decalindiol, 2-ethyl-1,3-hexanediol, 2,4-diethyloctane-1,3-diol, hydroquinone, bisphenol A, bisphenol F, bisphenol B, bisphenol S, 2,2-bis(4-hydroxycyclohexyl)propane, 1,1-, 1,2-, 1,3- and 1,4-cyclohexanedimethanol, and 1,2-, 1,3- or 1,4-cyclohexanediol. These compounds may be prepared, for example, by reacting said diols with an excess of, for example, the above-recited carbonates RO(CO)OR or chlorocarbonic esters, so that the dicarbonates thus obtained are substituted on both sides by groups RO(CO)—. A further possibility is to react the diols first with phosgene to give the corresponding chlorocarbonic esters of the diols, and then to react these esters with alcohols.

Further compounds (A1) are dicarboxylic acids, esters of dicarboxylic acids, preferably the methyl, ethyl, isopropyl, n-propyl, n-butyl, isobutyl, sec-butyl or tert-butyl esters, more preferably the methyl, ethyl or n-butyl esters. Examples of dicarboxylic acids of this kind are oxalic acid, maleic acid, fumaric acid, succinic acid, glutaric acid, adipic acid, sebacic acid, dodecanedioic acid, o-phthalic acid, isophthalic acid, terephthalic acid, azelaic acid, 1,4-cyclohexanedicarboxylic acid or tetrahydrophthalic acid, suberic acid, phthalic anhydride, tetrahydrophthalic anhydride, hexahydrophthalic anhydride, tetrachlorophthalic anhydride, endomethylenetetrahydrophthalic anhydride, glutaric anhydride, dimeric fatty acids, isomers thereof and hydrogenation products thereof.

The simplest structure of the condensation product (K), illustrated using, as example, the reaction of a carbonate (A) with a dialcohol or polyalcohol (B), produces the arrangement $XY_m$ or $Y_mX$, X being a carbonate or carbamoyl group, Y a hydroxyl group, and m generally an integer greater than 1 to 6, preferably greater than 1 to 4, more preferably greater than 1 to 3. The reactive group, which results as a single group, is generally referred to below as "focal group".

Where, for example, in the preparation of the simplest condensation product (K) from a carbonate and a dihydric alcohol, the molar reaction ratio is 1:1, then the result on average is a molecule of type XY, illustrated by the general formula (I).

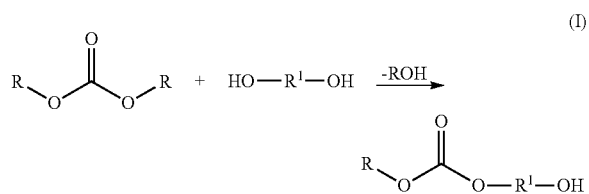

(I)

In the case of the preparation of the condensation product (K) from a carbonate and a trihydric alcohol with a molar reaction ratio of 1:1, the result on average is a molecule of type $XY_2$, illustrated by the general formula (II). The focal group here is a carbonate group.

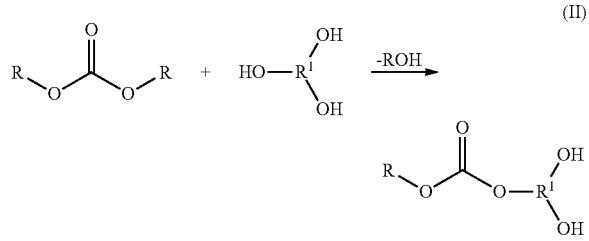

(II)

In the preparation of the condensation product (K) from a carbonate and a tetrahydric alcohol, again with the molar reaction ratio 1:1, the result on average is a molecule of type $XY_3$, illustrated by the general formula (III). The focal group here is a carbonate group.

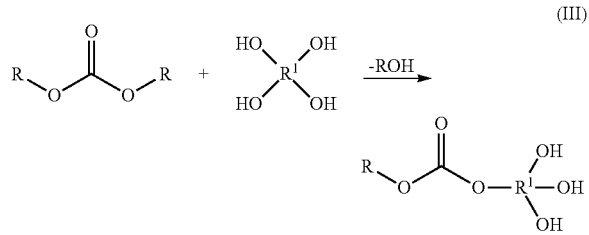

(III)

In the formulae (I) to (III) R is as defined at the outset and $R^1$ is an aliphatic or aromatic radical.

The condensation product (K) can also be prepared, for example, from a carbonate and a trihydric alcohol, illustrated by the general formula (IV), where the reaction ratio on a molar basis is 2:1. Here the result on average is a molecule of type $X_2Y$, the focal group here being an OH group. In the formula (IV) the definitions of R and $R^1$ are the same as above in formulae (I) to (III).

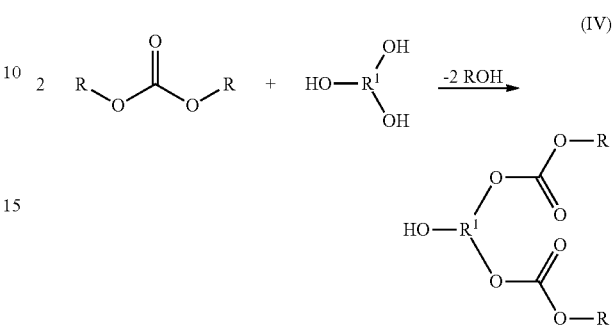

(IV)

Where difunctional compounds, e.g., a dicarbonate or a diol, are additionally added to the components, this produces an extension of the chains, as illustrated for example in the general formula (V). The result again is on average a molecule of type $XY_2$, the focal group being a carbonate group.

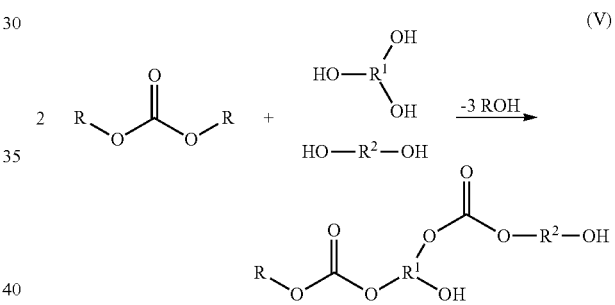

(V)

In formula (V) $R^2$ is an aliphatic or aromatic radical while R and $R^1$ are defined as described above.

It is also possible to use two or more condensation products (K) for the synthesis. In this case it is possible on the one hand to use two or more alcohols and/or two or more carbonates. Furthermore, through the choice of the ratio of the alcohols and carbonates or phosgenes used, it is possible to obtain mixtures of different condensation products with different structure. This may be exemplified taking, as example, the reaction of a carbonate with a trihydric alcohol. If the starting products are used in a 1:1 ratio, as depicted in (II), a molecule $XY_2$ is obtained. If the starting products are used in a 2:1 ratio, as illustrated in (IV), the result is a molecule $X_2Y$. With a ratio between 1:1 and 2:1 a mixture of molecules $XY_2$ and $X_2Y$ is obtained.

Typical reaction conditions for the reaction of (A) with (B) to form the condensation product (K) are set out below:

The stoichiometry of components (A) and (B) is generally chosen such that the resultant condensation product (K) contains either one carbonate or carbamoyl chloride group and more than one OH group, or one OH group and more than one carbonate or carbamoyl chloride group. This is achieved in the first case by a stoichiometry of 1 mol of carbonate groups: >2 mol of OH groups, for example, a stoichiometry of 1:2.1 to 8, preferably 1:2.2 to 6, more preferably 1:2.5 to 4, and very preferably 1:2.8 to 3.5. In the second case it is achieved by a stoichiometry of more than 1 mol of carbonate groups: <1 mol of OH groups, for example, a stoichiometry of 1:0.1 to 0.48, preferably 1:0.15 to 0.45, more preferably 1:0.25 to 0.4, and very preferably 1:0.28 to 0.35.

The temperature ought to be sufficient for the reaction of the alcohol with the corresponding carbonyl component. For the reaction with a phosgene a sufficient temperature is generally from −20° C. to 120° C., preferably 0 to 100° C., and more preferably 20 to 80° C. When a carbonate is used the temperature should be 60 to 280° C., preferably 80 to 250° C., more preferably 100 to 250° C., and very preferably 120 to 250° C.

Preparation takes place usually in a pressure range from 0.1 mbar to 20 bar, preferably at 1 mbar to 5 bar, in reactors or reactor cascades, which are operated batchwise, semibatchwise or continuously.

Solvents contemplated include aromatic and/or (cyclo) aliphatic hydrocarbons and mixtures thereof, halogenated hydrocarbons, ketones, esters, and ethers, preferably butyl acetate, dimethylformamide, dimethylacetamide, dimethyl sulfoxide, methoxy-propyl acetate, isobutyl methyl ketone, 2-butanone, aromatic hydrocarbons (such as Solvesso® products), cyclohexane, chlorobenzene, and xylene. A preferred embodiment is to carry out the reaction without solvent.

The order in which the individual components are added is generally of minor importance. As a general rule it is sensible to introduce the excess component of the two reaction partners first and to add the deficit component. Alternatively it is likewise possible to mix the two components with one another before the beginning of reaction and then to heat this mixture to the requisite reaction temperature.

The simple condensation products (K) described exemplarily in formulae (I)-(V) undergo in accordance with the invention preferably immediate intermolecular further reaction to form high-functionality polycondensation products, referred to below as polycondensation products (P). The reaction to give the condensation product (K) and to give the polycondensation product (P) takes place usually at a temperature of 0 to 300° C., preferably 0 to 250° C., more preferably at 60 to 250° C., and very preferably at 80 to 250° C., in bulk (without solvent) or in solution. In this context it is possible generally to use any solvents which are inert toward the respective reactants. Preference is given to using organic solvents, such as those mentioned above, for example, and more preferably decane, dodecane, cyclohexane, benzene, toluene, chlorobenzene, xylene, dimethylformamide, dimethylacetamide, dimethyl sulfoxide or solvent naphtha. In one preferred embodiment the condensation reaction is carried out in bulk. The monofunctional alcohol or the phenol which is liberated during the reaction, ROH, can be removed from the reaction equilibrium in order to accelerate the reaction, such removal taking place, for example, by distillative means, optionally under reduced pressure.

The separation of the alcohol or phenol can also be assisted by passing through the reaction mixture a stream of gas which is substantially inert under the reaction conditions (i.e., stripping), such as, for example, nitrogen, steam, carbon dioxide, or else by passing through the mixture an oxygen-containing gas, such as atmospheric air or lean air, for example. If distillative removal is intended, it is advisable as a general rule to use carbonates which during the reaction give off alcohols or phenols ROH having a boiling point of less than 140° C. under the prevailing pressure. Alternatively the alcohols liberated may be removed by azeotropic distillation using azeotrope formers (e.g., toluene, xylene, chlorobenzene, cyclohexane) or by application of a vacuum, such removal supporting the formation of the polycondensate.

To accelerate the reaction it is also possible to add catalysts or catalyst mixtures. Suitable catalysts are compounds which catalyze esterification or transesterification reactions, examples being alkali metal hydroxides, alkali metal carbonates, alkali metal hydrogen carbonates, preferably of sodium, of potassium or of cesium, tertiary amines, guanidines, ammonium compounds, phosphonium compounds, organoaluminum, organotin, organozinc, organotitanium, organozirconium or organobismuth compounds, and also catalysts of the kind known as double metal cyanide (DMC) catalysts, as described, for example, in DE 10138216 or in DE 10147712. Preference is given to using potassium hydroxide, potassium carbonate, potassium hydrogen carbonate, diazabicyclooctane (DABCO), diazabicyclononene (DBN), diazabicycloundecene (DBU), imidazoles, such as imidazole, 1-methylimidazole or 1,2-dimethylimidazole, titanium tetrabutoxide, titanium tetraisopropoxide, dibutyltin oxide, dibutyltin dilaurate, tin dioctoate, zirconium acetylacetonate, or mixtures thereof. The catalyst is generally added in an amount of 50 to 10,000 ppm by weight, preferably of 100 to 5000 ppm by weight, based on the amount of alcohol or alcohol mixture employed. It may optionally be necessary to predissolve the catalyst in small amounts of a suitable solvent.

Furthermore it is also possible, either by adding the appropriate catalyst and/or by choosing a suitable temperature, to control the intermolecular polycondensation reaction. In addition the average molecular weight of the polymer (P) can be adjusted via the composition of the starting components and via the residence time.

The condensation products (K) and the polycondensation products (P), which have been prepared at an elevated temperature, are stable at room temperature usually for a relatively long period of time, for example, for at least 6 weeks, without displaying turbidities, precipitations and/or any increase in viscosity. In view of the nature of the condensation products (K) it is possible that the condensation reaction may result in polycondensation products (P) having different structures, with branches but no crosslinks. Furthermore, the polycondensation products (P) ideally contain either a carbonate or carbamoyl chloride focal group and more than two OH groups, or else an OH focal group and more than two carbonate or carbamoyl chloride groups. The number of reactive groups depends on the nature of the condensation products (K) employed and on the degree of polycondensation.

For example, a condensation product (K) of the general formula (II) may react by triple intermolecular condensation to form two different polycondensation products (P), which are reproduced in general formulae (VI) and (VII).

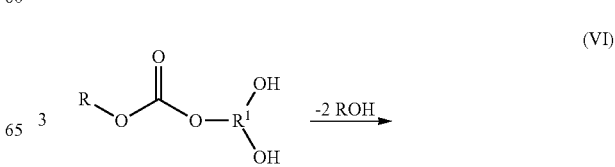

(VI)

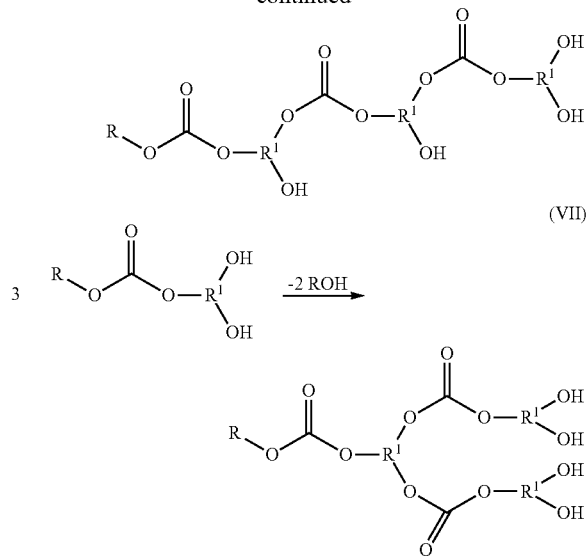

R and R¹ in formulae (VI) and (VII) are as defined above.

To terminate the intermolecular polycondensation reaction there are a variety of possibilities. By way of example the temperature can be lowered to a range in which the reaction comes to a standstill and the product (K) or the polycondensation product (P) is stable on storage. This is generally the case at below 60° C., preferably below 50° C., more preferably below 40° C., and very preferably at room temperature. Furthermore, the catalyst can be deactivated: in the case of basic catalysts, for example, by adding an acidic component, a Lewis acid for example, or an organic or inorganic protic acid. A further possibility is to arrest the reaction by dilution with a precooled solvent. This is particularly preferred when it is necessary to adapt the viscosity of the reaction mixture by adding solvent.

In a further embodiment, as soon as the intermolecular reaction of the condensation product (K) gives a polycondensation product (P) having the desired degree of polycondensation, the reaction can be arrested by adding to the product (P) a product having groups that are reactive toward the focal group of (P). For instance, in the case of a carbonate or carbamoyl focal group, a mono-, di- or polyamine, for example, can be added. In the case of a hydroxyl focal group, the product (P) can have added to it, for example, a mono-, di- or polyisocyanate, a compound comprising epoxide groups, or an acid derivative which is reactive with OH groups.

As a result of the aforementioned setting of the reaction conditions and optionally as a result of the choice of suitable solvent, the products of the invention can be processed further following preparation, without additional purification. If necessary, the reaction mixture can be subjected to decoloring, by means for example of treatment with activated carbon or metal oxides, such as alumina, silica, magnesium oxide, zirconium oxide, boron oxide or mixtures thereof, in amounts for example of 0.1%-50%, preferably 0.5% to 25%, more preferably 1%-10%, by weight, at temperatures of, for example, 10 to 100° C., preferably 20 to 80° C., and more preferably 30 to 60° C. It is also optionally possible to filter the reaction mixture in order to remove any precipitates present. In a further preferred embodiment the product is stripped, i.e., freed from volatile compounds of low molecular weight. For this purpose, after the desired degree of conversion has been reached, the catalyst can be optionally deactivated and the volatile constituents of low molecular weight, such as monoalcohols, phenols, carbonates, hydrogen chloride or volatile oligomeric or cyclic compounds, can be removed by distillation, optionally accompanied by introduction of a gas, preferably nitrogen, carbon dioxide or air, optionally under reduced pressure.

The hyperbranched polycarbonates obtainable as described above generally have a glass transition temperature of less than 50° C., preferably less than 30 and more preferably less than 10° C. The OH number is usually at least 30 mg KOH/g, preferably between 50 and 250 mg/g. The weight-average molar weight $M_w$ is usually between 1000 and 150,000, preferably from 1500 to 100,000 g/mol, the number-average molar weight $M_n$ between 500 and 50,000, preferably between 1000 and 40,000 g/mol. The hyperbranched polycarbonate is usually not soluble or dispersible in water, i.e., it is not possible to prepare a clear (i.e., devoid of particles visible to the naked eye) aqueous solution or dispersion.

The amphiphile preferably comprises an alkoxylated hyperbranched polycarbonate. The term "alkoxylated" means that the hyperbranched polycarbonate has been reacted with an alkylene oxide. As a result, the polycarbonate comprises at least one linear polyalkylene oxide group. Random mixtures or block of the monomers may occur, preferably blocks. The alkoxylated polycarbonate is preferably alkoxylated either exclusively with ethylene oxide or else with a mixture of ethylene oxide and $C_3$-$C_5$ alkylene oxide. It is more preferably alkoxylated exclusively with ethylene oxide. Suitable $C_3$-$C_5$ alkylene oxides are propylene oxide, butylene oxide or pentylene oxide, and mixtures thereof. A preferred $C_3$-$C_5$ alkylene oxide is propylene oxide. Mixtures of ethylene oxide and $C_3$-$C_5$ alkylene oxide preferably comprise at least 40 mol % of ethylene oxide, more preferably at least 60 mol % and especially at least 80 mol %, based in each case on the total number of moles of ethylene oxide and $C_3$-$C_5$ alkylene oxide in the mixture. The alkoxylated polycarbonate is more preferably alkoxylated with a mixture of ethylene oxide and $C_3$-$C_5$ alkylene oxide, which gives blocks of ethylene oxide and of $C_3$-$C_5$ alkylene oxide.

In a further preferred embodiment, the polycarbonate comprises at least one polyalkylene oxide group prepared by alkoxylation. The polyalkylene oxide group more preferably comprises at least one polyethylene oxide block and at least one poly($C_3$-$C_5$ alkylene oxide) block, the latter preferably being polypropylene oxide. The poly($C_3$-$C_5$ alkylene oxide) block is especially preferably bonded directly to the hyperbranched polycarbonate. The polyethylene oxide block is especially preferably not bonded directly to the polycarbonate, but exclusively to the poly($C_3$-$C_5$ alkylene oxide). Suitable $C_3$-$C_5$ alkylene oxides for the poly($C_3$-$C_5$ alkylene oxide) are as described above. The block structures are obtainable by first alkoxylating the hyperbranched polycarbonate with $C_3$-$C_5$ alkylene oxide and then alkoxylating the reaction product thus obtained with ethylene oxide.

The weight ratio of the sum of $C_3$-$C_{12}$ alkylene oxide (resulting from the at least trifunctional or higher polyfunctional polyetherol) and $C_3$-$C_5$ alkylene oxide (resulting from the alkoxylation of the hyperbranched polycarbonate) to ethylene oxide is usually in the range from 3:1 to 1:3, preferably in the range from 2.5:1 to 1:2.5 and especially from 2:1 to 1:2. The alkoxylation of the polycarbonate can be effected by the process according to the invention for preparing the amphiphile.

The alkoxylated hyperbranched polycarbonate is preferably water-soluble. This means that it is soluble in water at 20° C. to an extent of at least 2% by weight, preferably 8% by weight and especially to an extent of at least 15% by weight.

In a further embodiment, the alkoxylated hyperbranched polycarbonate is usually water-dispersible. This means that it is dispersible in water at 20° C. to an extent of at least 2% by weight, preferably 8% by weight and especially to an extent of at least 15% by weight.

The alkoxylated hyperbranched polycarbonate usually has an OH number of 1 to 150 mg KOH per g of polymer, preferably 10 to 120 mg KOH/g, especially 20 to 100 mg KOH/g.

The inventive composition usually comprises 0.01 to 40% by weight, preferably 0.05 to 30% by weight, more preferably 0.1 to 20% by weight, of amphiphile.

The composition of the invention is obtainable by bringing the amphiphile and the active ingredient whose solubility in water at 20° C. is not more than 10 g/L into contact. The components can be brought into contact by methods which are common knowledge, such as mixing, emulsifying or suspending.

The weight ratio of active ingredient to amphiphile is usually in the range from 100:1 to 1:100, preferably 10:1 to 1:50, more preferably 2:1 to 1:25. The active ingredient may be in dissolved form or in solid, particulate form. The active ingredient particles may be crystalline or amorphous. The particle size may be 1 nm to 10 µm. The composition may be a solution, emulsion, suspension or suspoemulsion of the active ingredient. The composition of the invention is preferably an aqueous composition. Preferably it comprises at least 40%, more preferably at least 60%, and more particularly at least 80% by weight of water. The composition typically comprises not more than 99% by weight of water.

The composition of the invention may comprise formulating assistants, the choice of assistants being guided typically by the specific application form and/or active ingredient. Examples of suitable formulating assistants are solvents, solid carriers, surface-active substances (such as surfactants, protective colloids, wetting agents, and stickers), organic and inorganic thickeners, bactericides, antifreeze agents, defoamers, optionally colorants, and adhesives (e.g., for seed treatment).

Surface-active substances contemplated (adjuvants, wetting agents, stickers, dispersants or emulsifiers) include the alkali metal, alkaline earth metal, and ammonium salts of aromatic sulfonic acids, e.g., those of lignosulfonic (Borresperse® products, Borregaard, Norway), phenolsulfonic, naphthalenesulfonic (Morwet® products, Akzo Nobel, USA), and dibutylnaphthalenesulfonic (Nekal® products, BASF, Germany) acid, and also of fatty acids, alkyl- and alkylarylsulfonates, alkyl, lauryl ether, and fatty alcohol sulfates, and also salts of sulfated hexa, hepta-, and octadecanols and also of fatty alcohol glycol ethers, condensation products of sulfonated naphthalene and its derivatives with formaldehyde, condensation products of naphthalene or of naphthalenesulfonic acids with phenol and formaldehyde, polyoxyethylene octylphenol ethers, ethoxylated isooctylphenol, octylphenol or nonylphenol, alkyllphenyl and tributylphenyl polyglycol ethers, alkylaryl polyether alcohols, isotridecyl alcohol, fatty alcohol ethylene oxide condensates, ethoxylated castor oil, polyoxyethylene or polyoxypropylene alkyl ethers, lauryl alcohol polyglycol ether acetate, sorbitol esters, lignin-sulfite waste liquors, and also proteins, denatured proteins, polysaccharides (e.g., methylcellulose), hydrophobically modified starches, polyvinyl alcohol (Mowiol® products, Clariant, Switzerland), polycarboxylates (Sokalan® products, BASF, Germany), polyalkoxylates, polyvinylamine (Lupamin® products, BASF, Germany), polyethyleneimine (Lupasol® products, BASF, Germany), polyvinylpyrrolidone and copolymers thereof.

Suitable surfactants include, in particular, anionic, cationic, nonionic, and amphoteric surfactants, block polymers, and polyelectrolytes. Suitable anionic surfactants are alkali metal, alkaline earth metal or ammonium salts of sulfonates, sulfates, phosphates or carboxylates. Examples of sulfonates are alkylarylsulfonates, diphenylsulphonates, alpha-olefinsulfonates, sulfonates of fatty acids and oils, sulfonates of ethoxylated alkylphenols, sulfonates of condensed naphthalenes, sulfonates of dodecyl and tridecylbenzenes, sulfonates of naphthalenes and alkylnaphthalenes, sulfosuccinates or sulfosuccinamates. Examples of sulfates are sulfates of fatty acids and oils, of ethoxylated alkylphenols, of alcohols, of ethoxylated alcohols, or of fatty acid esters. Examples of phosphates are phosphate esters. Examples of carboxylates are alkyl carboxylates and carboxylated alcohol or alkylphenol ethoxylates.

Suitable nonionic surfactants are alkoxylates, N-alkylated fatty acid amides, amine oxides, esters or sugar-based surfactants. Examples of alkoxylates are compounds, such as alcohols, alkylphenols, amines, amides, arylphenols, fatty acids or fatty acid esters, which have been alkoxylated. For the alkoxylation it is possible to use ethylene oxide and/or propylene oxide, preferably ethylene oxide. Examples of N-alkylated fatty acid amides are fatty acid glucamides or fatty acid alkanolamides. Examples of esters are fatty acid esters, glycerol esters or monoglycerides. Examples of sugar-based surfactants are sorbitans, ethoxylated sorbitans, sucrose esters and glucose esters, or alkylpolyglucosides. Suitable cationic surfactants are quaternary surfactants, examples being quaternary ammonium compounds having one or two hydrophobic groups, or salts of long-chain primary amines. Suitable amphoteric surfactants are alkylbetaines and imidazolines. Suitable block polymers are block polymers of A-B or A-B-A type, comprising blocks of polyethylene oxide and polypropylene oxide, or of A-B-C type, comprising alkanol, polyethylene oxide, and polypropylene oxide. Suitable polyelectrolytes are polyacids or polybases. Examples of polyacids are alkali metal salts of polyacrylic acid. Examples of polybases are polyvinylamines or polyethylenamines.

The composition of the invention may comprise large amounts of surface-active substances and surfactant. It may comprise 0.1% to 40%, preferably 1% to 30% and more particularly 2% to 20% by weight in total amount of surface-active substances and surfactants, based on the total amount of the composition.

Examples of adjuvants are organically modified polysiloxanes, such as BreakThruS 240®; alcohol alkoxylates, such as Atplus®245, Atplus®MBA 1303, Plurafac®LF, and Lutensol® ON; EO-PO block polymers, e.g., Pluronic® RPE 2035 and Genapol® B; alcohol ethoxylates, e.g., Lutensol® XP 80; and sodium dioctylsulfosuccinate, e.g., Leophen® RA.

Examples of thickeners (i.e., compounds which give the composition a modified rheology, i.e., high viscosity in the state of rest and low viscosity in the mobile state) are polysaccharides and also organic and inorganic layer minerals such as xanthan gum (Kelzan®, CP Kelco), Rhodopol® 23 (Rhodia) or Veegum® (R.T. Vanderbilt) or Attaclay® (Engelhard Corp.).

In one preferred embodiment the active compound is a pesticide and the compositions of the invention are in the form of an agrochemical formulation. Suitable agrochemical formulations are water-soluble concentrates (SL, LS), redispersible concentrates (DC), emulsifiable concentrates (EC), emulsions (EW, EO, ES, ME), suspensions (SC, OD, FS) or suspoemulsions (SE). The composition preferably takes the form of an emulsifiable concentrate (EC), a suspension concentrate (SC), a water-soluble concentrate (SL), a solution for seed treatment (LS), or a redispersible concentrate (DC).

The agrochemical formulation is usually diluted prior to application, to prepare what is known as a tankmix. Suitable agents for the dilution include mineral oil fractions of moderate to high boiling point, such as kerosene or diesel oil, and also coal tar oils and oils of vetable or animal origin, aliphatic, cyclic, and aromatic hydrocarbons, e.g., toluene, xylene, paraffin, tetrahydronaphthalene, alkylated naphthalenes or derivatives thereof, methanol, ethanol, propanol, butanol, cyclohexanol, cyclohexanone, isophorone, strongly polar solvents, e.g., dimethyl sulfoxide, N-methylpyrrolidone or water. It is preferred to use water. It is also possible to add the amphiphile only to the actual tankmix. In this embodiment the composition of the invention is in the form of a tankmix.

The diluted composition is typically applied by spraying or nebulizing. To the tankmix it is possible to add oils of various types, wetting agents, adjuvants, herbicides, bactericides or fungicides immediately prior to application (tankmix). These agents may be admixed to the compositions of the invention in a weight ratio of 1:100 to 100:1, preferably 1:10 to 10:1. The concentration of pesticide in the tankmix may be varied within relatively wide ranges. Concentrations are in general between 0.0001% and 10%, preferably between 0.01% and 1%. In the case of application in crop protection, and depending on the nature of the desired effect, the application rates are between 0.01 and 2.0 kg of active ingredient per ha.

The agrochemical formulations can be used to control phytopathogenic fungi and/or unwanted plant growth and/or unwanted insect or mite infestation and/or to regulate the growth of plants, the composition then being caused to act on the respective pests, their habitat, or the plants to be protected from the respective pest, the soil, and/or on unwanted plants and/or on the crop plants and/or on their habitat. The agrochemical formulations can also be used to control unwanted insect or mite infestation on plants and/or to control phytopathogenic fungi and/or to control unwanted plant growth, with seeds of crop plants being treated with the composition.

The invention also provides an amphiphile comprising an alkoxylated hyperbranched polycarbonate, wherein the polycarbonate comprises an alcohol (B1) which is a trifunctional or higher polyfunctional polyetherol based on a $C_3$-$C_{12}$ alkylene oxide and an alcohol which has at least three OH groups. The amphiphile is obtainable, and is preferably obtained, by the inventive preparation process as described below. The polyetherol preferably comprises at least three $C_3$-$C_{12}$ alkylene oxide molecules in polymerized form. The alkoxylated polycarbonate is preferably alkoxylated with ethylene oxide or a mixture of ethylene oxide and $C_3$-$C_5$ alkylene oxide. Other suitable and preferred embodiments have been described above.

The invention also relates to a process for preparing the inventive amphiphile, by alkoxylating a hyperbranched polycarbonate, wherein the polycarbonate comprises an alcohol (B1) which is a trifunctional or higher polyfunctional polyetherol based on a $C_3$-$C_{12}$ alkylene oxide and an alcohol which has at least three OH groups. The polycarbonate is preferably alkoxylated using ethylene oxide or a mixture of ethylene oxide and $C_3$-$C_5$ alkylene oxide. The weight ratio of the sum of $C_3$-$C_{12}$ alkylene oxide and $C_3$-$C_5$ alkylene oxide to ethylene oxide is usually in the range from 3:1 to 1:3. The polycarbonate is more preferably alkoxylated first with $C_3$-$C_5$ alkylene oxide and then with ethylene oxide.

The alkoxylation can be performed by the customary reaction processes, for example in a pressure autoclave. The alkoxylation can be catalyzed by strong bases, such as alkali metal hydroxides and alkaline earth metal hydroxides, Brønsted or Lewis acids, such as $AlCl_3$, $BF_3$, etc. For narrow-distribution alkoxylates, catalysts such as hydrotalcite or DMC can be used. The alkoxylation is effected preferably at temperatures in the range from about 80 to 250° C., preferably about 100 to 220° C. The pressure is preferably between ambient pressure and 600 bar. If desired, the alkylene oxide may comprise an addition of inert gas, for example of about 5 to 60%. The crude product of the alkoxylation can be used without further work up in the inventive composition. It can optionally be filtered, for example to remove catalyst residues.

The invention additionally provides for the use of the inventive amphiphile for solubilizing an active ingredient whose solubility in water at 20° C. is not more than 10 g/L, in aqueous solutions.

The invention further relates to a method of controlling phytopathogenic fungi and/or unwanted plant growth and/or unwanted insect or mite infestation and/or of regulating the growth of plants, wherein the inventive composition is caused to act on the respective pests, their habitat, or the plants to be protected from the respective pest, the soil, and/or on unwanted plants and/or on the crop plants and/or on their habitat. The invention also relates to a use of the inventive composition for controlling phytopathogenic fungi and/or unwanted plant growth and/or unwanted insect or mite infestation and/or for regulating the growth of plants.

Advantages of the present invention are that a high concentration of active ingredient can be brought into solution; that the preparation of the amphiphile from commercially readily available monomers can be accomplished very easily and industrially, optionally even in a one-pot process. A further advantage is that the amphiphile itself is water-soluble or water-dispersible, and that it is less sensitive to hydrolysis than are many polyesters. Further advantages are that the bioavailability of the active ingredients is increased, that the systemic effect of the active agrochemical ingredients is increased on foliar uptake, that even sparingly soluble active agrochemical ingredients can now be formulated in solution, for example as an SL (water-soluble concentrate) or LS (solution for seed treatment), that the distribution of the active agrochemical ingredients in the spraying solution is improved, and that the multiple-use packaging of the active ingredients, and the application equipment (e.g., the spraying equipment for pesticides), can be cleaned more effectively with water.

The examples which follow illustrate the invention without restricting it.

EXAMPLES

Both the unmodified hyperbranched polycarbonates and the alkoxylated polycarbonates were analyzed by gel permeation chromatography using a refractometer as detector. The mobile phase used was dimethylacetamide, while the standard used for determining the molecular weight was polymethyl methacrylate (PMMA). The OH number was determined in accordance with DIN 53240, part 2.

Example 1A

Synthesis of Hyperbranched Polycarbonate Core with Terminal Hydroxyl Groups 2000 g of TMP×15.7 PO (reaction product of trimethylolpropane with 15.7 molar excess of propylene oxide), 247 g of diethyl carbonate and 1.7 g of di-n-butyltin dilaurate catalyst were initially charged. The reaction mixture was heated to 165° C. and kept at boiling with stirring for 13 hours, until the temperature of the reaction mixture had fallen to a constant temperature of 143° C. as a result of the evaporative cooling of the ethanol being released. The reflux condenser was then replaced by a descending condenser with a collecting vessel, and the ethanol formed in the reaction was distilled off, in the course of which the temperature of the reaction mixture was increased up to 230° C. The ethanol was collected in a cooled round-bottom flask and weighed, and the conversion was thus determined as a percentage compared to the theoretically possible full conversion. After the attainment of a conversion of 89%, dry nitrogen was passed through the reaction mixture at a temperature of 160° C. for 3 hours, in order to remove residual amounts of monomers still present. Thereafter, the mixture was cooled to room temperature. The polymer (Mn=3000 g/mol; Mw=6200 g/mol; OH number: 87 mg KOH/g polymer) was obtained in the form of a yellow, high-viscosity liquid which was water-insoluble.

Example 1B

Synthesis of Hyperbranched Polycarbonate Core with Terminal Hydroxyl Groups 4010 g of TMP×15.7 PO (reaction product of trimethylolpropane with 15.7 molar excess of propylene oxide) and 502 g of diethyl carbonate were initially charged and admixed with a freshly made-up solution of 2 g of potassium hydroxide in 10 g of ethanol. The reaction mixture was heated to 155° C. and kept at boiling with stirring for 3.5 hours, until the temperature of the reaction mixture had fallen to a constant temperature of 130° C. as a result of the evaporative cooling of the ethanol being released. Then the reflux condenser was replaced by a descending condenser with collecting vessel, and the ethanol formed in the reaction was distilled off, in the course of which the temperature was increased up to 200° C. The ethanol was collected in a cooled round-bottom flask and weighed, and the conversion was thus determined as a percentage compared to the theoretically possible full conversion. After the attainment of a conversion of 80%, the reaction was cooled to 100° C. and admixed with 4 g of 80% phosphoric acid as a stopper. Subsequently, the mixture was heated to 135° C. with stirring, and dry nitrogen was passed through the reaction mixture at this temperature for 5 hours in order to remove residual amounts of monomers still present. Thereafter, the mixture was cooled to room temperature. The polymer (Mn=2450 g/mol; Mw=5330 g/mol; OH number: 92 mg KOH/g polymer) was obtained in the form of a yellow, high-viscosity liquid which was water-insoluble.

Example 1C

Ethoxylation of Hyperbranched Polycarbonate Core from Example 1A 100 g of polymer from example 1A were initially charged in a pressure autoclave and admixed with 1.35 g of a 50% aqueous KOH solution. Once the reaction mixture had been inertized with nitrogen, the mixture was freed of water residues at 120° C. under reduced pressure. Subsequently, 100 g of ethylene oxide were added to the reaction mixture with a metering rate of 0.5 ml/min at 120° C. After the metered addition of ethylene oxide had ended and a constant reactor pressure had been attained, unconverted ethylene oxide and other volatile constituents were distilled off under reduced pressure and the ethoxylated polymer was removed from the polymerization reactor. Subsequently, the crude product was admixed in a separate reaction apparatus with 5% Makrosorb® (PQ Corp.; magnesium silicate to remove alkali residues) and 2% water, and heated to 80° C. for 1 hour, and the water added was subsequently distilled out of the reaction mixture again under reduced pressure. The filtration of the crude product gave 190 g of ethoxylated polymer (Mn=4860 g/mol; Mw=12 980 g/mol; OH number: 47 mg KOH/g polymer) in the form of a slightly yellow, high-viscosity liquid which was completely water-soluble.

Example 2

Solubilization of Active Ingredients 100 mg of polymer were weighed out into a 50 mL glass beaker and dissolved in 9.900 g of distilled water. Then 100 mg of each active ingredient was weighed into the batch to give a supersaturated solution. The mixture was then stirred at room temperature for 24 hours, using a drum mixer. After a rest time of one hour, unsolubilized active ingredient was removed by centrifuging. The resulting clear solution was then analyzed for its active ingredient content by means of UV spectroscopy. The active ingredients were analyzed at the following wavelengths: pyrene at 334 nm, pyraclostrobin at 277 nm, fipronil at 280 nm.

TABLE 1

| | Solubility [mg/l] in the presence of | | |
|---|---|---|---|
| | Pyrene | Pyraclostrobin | Fipronil |
| Without polymer[a] | 0.1 | 22.5 | 3 |
| Polymer from example 1[a] | —[b] | —[b] | —[b] |
| Polymer from example 2 | 22 | 95 | 8 |

[a] not inventive;
[b] 100 mg of polymer did not dissolve in 9.9 g of water.

The invention claimed is:

1. A composition comprising an active ingredient whose solubility in water at 20° C. is not more than 10 g/L, and an alkoxylated hyperbranched polycarbonate, wherein the polycarbonate comprises a propoxylated alcohol containing 3 to 30 propylene oxide molecules in polymerized form, wherein the propoxylated alcohol is selected from glycerol, trimethylolpropane, 1,2,4-butanetriol, 1,2,3-hexanetriol, 1,2,4-hexanetriol and pentaerythritol, wherein the alkoxylated polycarbonate is alkoxylated with ethylene oxide, and wherein the weight ratio of the propylene oxide to the ethylene oxide is in the range from 3:1 to 1:3.

2. The composition according to claim 1, wherein the active ingredient comprises an active agrochemical ingredient, active cosmetic ingredient, active pharmaceutical ingredient or nutritional supplement.

3. The composition according to claim 1, wherein the active ingredient is an active agrochemical ingredient.

4. An amphiphile comprising an alkoxylated hyperbranched polycarbonate, wherein the polycarbonate comprises a propoxylated alcohol containing 3 to 30 propylene oxide molecules in polymerized form, wherein the propoxylated alcohol is selected from glycerol, trimethylolpropane, 1,2,4-butanetriol, 1,2,3-hexanetriol, 1,2,4-hexanetriol and pentaerythritol, wherein the alkoxylated polycarbonate is alkoxylated with ethylene oxide, and wherein the weight ratio of the propylene oxide to the ethylene oxide is in the range from 3:1 to 1:3.

5. A process for preparing the amphiphile according to claim 4, comprising alkoxylating a hyperbranched polycarbonate using ethylene oxide, wherein the polycarbonate comprises propoxylated alcohol containing 3 to 30 propylene oxide molecules in polymerized form, wherein the propoxylated alcohol is selected from glycerol, trimethylolpropane, 1,2,4-butanetriol, 1,2,3-hexanetriol, 1,2,4-hexanetriol and pentaerythritol.

6. A method for solubilizing an active ingredient, whose solubility in water at 20° C. is not more than 10 g/L, in aqueous solutions, comprising the admixing the active ingredient with the amphiphile according to claim 4 in an aqueous solution.

7. A method of controlling phytopathogenic fungi, unwanted plant growth, or unwanted insect or mite infestation, or of regulating the growth of plants, the composition according to claim 1 is allowed to act on the respective pests, their habitat, or the plants to be protected from the respective pest, the soil, or on unwanted plants or on the crop plants, or on their habitat.

8. The composition of claim 1, wherein the alcohol which has at least three OH groups is trimethylolpropane.

9. The composition of claim 1, wherein the weight ratio of propylene oxide to ethylene oxide is in the range from 2.5:1 to 1:2.5.

10. The composition of claim 4, wherein the alcohol which has at least three OH groups is trimethylolpropane.

11. The composition of claim 4, wherein the weight ratio of propylene oxide to ethylene oxide is in the range from 2.5:1 to 1:2.5.

* * * * *